(12) United States Patent
Ratilainen et al.

(10) Patent No.: US 8,816,119 B2
(45) Date of Patent: Aug. 26, 2014

(54) ARYLAMIDE DERIVATIVES HAVING ANTIANDROGENIC PROPERTIES

(75) Inventors: Jari Ratilainen, Kulho (FI); Milla Koistinaho, Paukarlahti (FI); Anu Muona, Harjamaki (FI)

(73) Assignee: Medeia Therapeutics Ltd, Kuoplo (FI)

( * ) Notice: Subject to any disclaimer, the term of this patent is extended or adjusted under 35 U.S.C. 154(b) by 0 days.

(21) Appl. No.: 13/809,787

(22) PCT Filed: Jul. 14, 2011

(86) PCT No.: PCT/FI2011/050655
§ 371 (c)(1),
(2), (4) Date: Jan. 11, 2013

(87) PCT Pub. No.: WO2012/007644
PCT Pub. Date: Jan. 19, 2012

(65) Prior Publication Data
US 2013/0109750 A1    May 2, 2013

(30) Foreign Application Priority Data
Jul. 15, 2010  (FI) .................................... 20105806

(51) Int. Cl.
C07C 255/03    (2006.01)
A61K 31/136    (2006.01)

(52) U.S. Cl.
USPC ........................ 558/413; 558/303; 514/676

(58) Field of Classification Search
USPC ................... 558/303, 413; 514/676
See application file for complete search history.

(56) References Cited

U.S. PATENT DOCUMENTS

| 4,636,505 A | 1/1987 | Tucker |
| 2006/0241180 A1* | 10/2006 | Dalton et al. ................ 514/521 |
| 2008/0188448 A1* | 8/2008 | Schwede et al. ............. 514/171 |

FOREIGN PATENT DOCUMENTS

WO    WO 2010/116342 A2    10/2010

OTHER PUBLICATIONS

International Search Report dated Nov. 16, 2011 issued in PCT/FI2011/050655.
Official Action dated Dec. 3, 2013 received from the Chinese Patent Office from the corresponding foreign Application No. 201180034245.0, together with an English-language translation.

* cited by examiner

*Primary Examiner* — Yong Chu
*Assistant Examiner* — Sonya Wright
(74) *Attorney, Agent, or Firm* — Scully, Scott, Murphy & Presser, P.C.

(57) ABSTRACT

The invention relates to novel arylamide derivatives having formula (I) and stereoisomers and pharmaceutically acceptable salts thereof, where R1-R11, R', R", z and X are as defined in the claims. The arylamide derivatives of formula (I) have antiandrogenic properties. The invention also relates to compounds of formula (I) for use as a medicament and to pharmaceutical compositions comprising them and to their preparation.

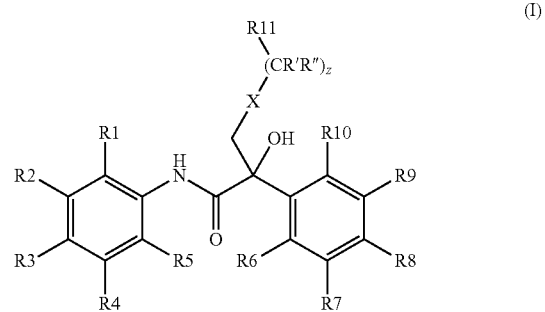

16 Claims, No Drawings

ARYLAMIDE DERIVATIVES HAVING ANTIANDROGENIC PROPERTIES

THE FIELD OF THE INVENTION

The present invention relates to new arylamide derivatives, their preparation, pharmaceutical compositions containing them and their use in the treatment of androgen receptor related disorders, such as benign prostate hyperplasia and cancer, particularly prostate cancer and/or castration-resistant prostate cancer.

BACKGROUND OF THE INVENTION

Androgens are produced by testes and adrenal glands and they play a critical role in the development and physiology of normal prostate. The etiology of benign prostate hyperplasia (BPH) and prostatic neoplasia which can progress to adenocarcinoma is androgen-dependent. Treatment of choice for BPH and prostate cancer (PCa) is reduction of androgen action in the prostate. In fact, almost 90% of men between ages 40-90 years develop either BPH or PCa. PCa is the second leading cause of cancer-related death and the most frequently diagnosed malignancy in men. PCa remains incurable in metastatic setting. As the incidence of PCa increases with age, the number of newly diagnosed cases rises continuously due to increased life expectancy of the population.

The conventional initial treatment for PCa is hormone or androgen deprivation therapy (ADT). Experimental ADT was first described already in 1941. ADT via surgical castration or by chemical castration using luteinizing hormone releasing hormone agonists is universally accepted first-line therapy in advanced PCa. See Perlmutter M, Lepor H. Androgen deprivation therapy in the treatment of advanced prostate cancer Rev Urol. 2007; 9(Suppl 1): S3-S8 and references therein.

Maximal androgen blockade is achieved by combining ADT with an anti-androgen treatment. Anti-androgens compete with endogenous androgens, testosterone and dihydrotestosterone, for binding in the ligand-binding pocket of the androgen receptor (AR). AR belongs to the superfamily of nuclear hormone receptors and is mainly expressed in reproductive tissues and muscles. Ligand binding to AR promotes its dissociation from heat shock proteins and other chaperones, leading to dimerization of the receptor, phosphorylation and subsequent translocation into the nucleus where AR binds to androgen responsive elements present in the regulatory regions of multiple genes involved in the growth, survival and differentiation of prostate cells.

The first non-steroidal anti-androgen, flutamide was approved for PCa in 1989 and the structurally related compounds, bicalutamide and nilutamide, were launched in 1995 and 1996, respectively. Non-steroidal compounds are more favorable than steroidal anti-androgens in clinical applications because of the lack of cross-reactivity with other steroid receptors and improved oral bioavailability. Of this structural class of propanamide anti-androgens, bicalutamide is the most potent, best tolerated and the leading anti-androgen on the market. Bicalutamide is described in patent literature for example in European patent EP 0100172. Certain arylamide derivatives have also been described in WO 2008/011072 A2 as selective androgen receptor modulators.

Unfortunately, although ADT and anti-androgen treatment typically result in early beneficial responses, PCa then progresses to a state where androgen deprivation fails to control the malignancy despite minimal testosterone levels. This state is termed castration-resistant prostate cancer (CRPC) (or hormone-refractory prostate cancer, HRPC) and is the lethal form of the disease. CRPC is believed to emerge after genetic and/or epigenetic changes in the prostate cancer cells and it is characterized by re-activation of the growth of cancer cells that have adapted to the hormone-deprived environment in the prostate.

The growth of cancer cells in CRPC remains dependent on the function of AR and studies over the past decade demonstrate that CRPC cells employ multiple mechanisms to re-activate AR. See Chen C D, Welsbie D S, Tran C. Baek S H, Chen R, Vessella R, Rosenfeld M G, Sawyers C L. Molecular determinants of resistance to antiandrogen therapy. Nat Med 2004 January; 10(1):33-39 and references therein. The major mechanisms include amplification of AR gene or up-regulation of AR mRNA or protein, point mutations in AR that allow activation of the AR by non-androgenic ligands or even anti-androgens, changes in the expression levels of co-activators and co-repressors of AR transcription, and expression of alternatively spliced and constitutively active variants of the AR. Thus, drugs targeting AR signaling could still be effective in the prevention and treatment of CRPC.

The limited utility of currently available anti-androgens is most likely related to an incomplete AR inhibition under certain circumstances (Taplin M E. Drug insight: role of the androgen receptor in the development and progression of prostate cancer. Nat Olin Pract Oncol, 2007 April; 4(4):236-244). Multiple molecular mechanisms may contribute to the failure of standard anti-androgen treatments. The use of anti-androgens that target ligand-binding domain of the AR, such as bicalutamide, can lead to selection of prostate cancer cells that harbor point mutations in the ligand-binding domain. In some cases these mutations can cause prostate cancer cells to convert antagonists to agonists. AR mutations are found in 10-40% of metastatic tumors. More than 70 mutations in the AR have been discovered, which result in increased basal activity of the receptor or widened ligand specificity.

For example, threonine to alanine mutation in amino acid 877 is the most frequently found mutation in PCa patients and converts flutamide, cyprotenone (steroidal anti-androgen), progesterone and estrogens agonistic in AR. Mutation in amino acid 741 from tryptophan to either leucine or cysteine accounts for the switch of bicalutamide from anti-androgen to an agonist (Hara T, Miyazaki J, Araki H, Yamaoka M, Kanzaki N, Kusaka M, Miyamoto M. Novel mutations of androgen receptor: a possible mechanism of bicalutamide withdrawal syndrome. Cancer Res. 2003 Jan. 1; 63(1):149-153.)

In addition to point mutations in AR, increased receptor levels can cause anti-androgens to function as agonists (Chen C D, Welsbie D S, Tran C, Baek S H, Chen R, Vessella R, Rosenfeld M G, Sawyers C L. Molecular determinants of resistance to antiandrogen therapy. Nat Med 2004 January; 10(1):33-39). The antagonist-agonist conversion has significant clinical relevance. Approximately 30% of men with progressing PCa experience a paradoxical drop in serum prostate specific antigen levels after discontinuation of the anti-androgen treatment.

To date, treatment for CRPC has been disappointing with expected survival estimated at 7-16 months and no significant improvement with currently available therapies. Effective, novel agents that target AR are therefore needed.

More specifically, there is a need for new anti-androgen compounds that are more potent than bicalutamide in antagonizing the activities of endogenous androgens on AR. There is also a need for new anti-androgen compounds that exhibit minimal agonism in AR. Importantly, there is a need for novel anti-androgens that do not gain agonistic activity in CRPC related mutant ARs or in CRPC related settings in which AR is present at high amounts. In addition, there is a need for non-steroidal, non-toxic molecules with drug-like properties that can be used in the treatment and prevention of BPH, PCa and CRPC.

Now it has been surprisingly found that the arylamide derivatives according to the present invention overcome the disadvantages related to bicalutamide.

SUMMARY OF THE INVENTION

The present invention provides new arylamide derivatives having formula (I)

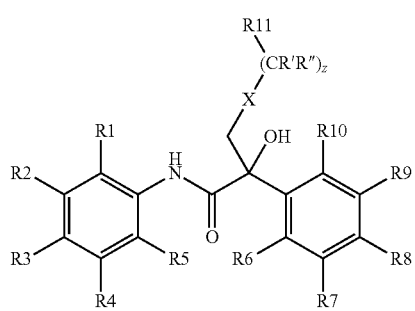

or pharmaceutically acceptable salts thereof or stereoisomers of Formula I; where R' and R" are each independently selected from the group consisting of H and alkyl;

z is an integer 0 to 3;

R1 is selected from the group consisting of H, halogen, (per)haloalkyl, hydroxy and $(CH_2)_n CHO$, where n is an integer 0-6;

R2 is selected from the group consisting of H, alkyl, halogen, trifluoromethyl, (halo)alkyl, hydroxy and $(CH_2)_n CHO$, where n is an integer 0-6;

R3 is selected from the group consisting of $NO_2$, CN, COR, COOH, CONHR, where R is hydrogen or alkyl; halogen and hydroxy;

R4 and R5 are each independently selected from the group consisting of H, alkyl and halogen, or R4 and R5 form together with the carbon atoms, to which they are attached, a substituted or unsubstituted aliphatic, heteroaliphatic, aromatic or heteroaromatic ring;

R6-R10 are each independently selected from the group consisting of H, alkyl, halogen, (per)haloalkyl, CN, $NO_2$, COR, COOH, CONHR, $NR_2$, $NHCOCH_3$, $NHCOCF_3$, NHCOR, NHCONHR, NHCOOR, OCONHR, CONHR, where R is as defined above; $NHCSCH_3$, alkylthio, alkylsulfinyl and alkylsulfonyl, provided that at least one of R6-R10 is other than H; or two adjacent R6-R10 form with the carbon atoms, to which they are attached, a substituted or unsubstituted aliphatic, heteroaliphatic, aromatic or heteroaromatic ring; X is selected from the group consisting of O, S, S(O), $SO_2$, NR12, where R12 is selected from the group consisting of H, alkyl, $COCH_3$ and COR, where R is as defined above; $CH_2$ and CO; or when z is 0, then X may be N and forms together with R11 a heterocyclic ring selected from the group consisting of morpholine, 1,2,4-triazole, imidazole and N-substituted imidazole; and R11, when not forming a ring with X as defined above, is selected from the group consisting of alkyl, alkenyl, (per)haloalkyl, haloalkenyl, alkyl-CN and an aryl, heteroaryl, aliphatic or heteroaliphatic, 5-7-membered ring optionally substituted with 1-5 substituents selected from the group consisting of alkyl, halogen, (per)haloalkyl, CN, $NO_2$, COR, COOH, CONHR, $NR_2$, $NHCOCH_3$, $NHCOCF_3$, NHCOR, NHCONHR, NHCOOR, OCONHR, $NHSO_2 R$, where R is as defined above; $NHCSCH_3$, alkylthio, alkylsulfinyl and alkylsulfonyl.

The invention also relates to pharmaceutical compositions comprising an effective amount of one or more arylamide derivatives of formula (I) or pharmaceutically acceptable salts thereof together with a suitable carrier and conventional excipients.

Further the invention relates to arylamide derivatives of formula (I) or pharmaceutically acceptable salts thereof for use as a medicament.

The invention also relates to arylamide derivatives of formula (I) or pharmaceutically acceptable salts thereof for use in the treatment of androgen receptor related diseases.

Finally the invention provides a process for preparing arylamide derivatives of formula (I).

DETAILED DESCRIPTION OF THE INVENTION

The arylamides of formula (I) according to the present invention possess at least one asymmetric carbon atom, i.e. the carbon atom, to which the hydroxyl is attached. Thus, the compounds exist in racemic form and optically active forms. All these forms are encompassed by the present invention.

By the term "alkyl", in the definition of the compound group of formula (I), is meant a linear or branched, saturated hydrocarbon chain containing 1 to 6 carbon atoms. The prefix "halo" means that such an alkyl group is halo-genated with e.g. fluoro, chloro, bromo or iodo, partially or completely (per)halo).

By the term "alkenyl" is meant an unsaturated hydrocarbon chain having one or more double bonds and containing 2 to 6 carbon atoms.

By the term "aliphatic, heteroaliphatic, aromatic or heteroaromatic ring" is meant a saturated or unsaturated, 4-7-membered ring, where 1-3 carbon atoms may be replaced by heteroatoms selected from O, S and N. Such a ring may be substituted with one or more substituents selected from the group consisting of alkyl, halogen, (per)haloalkyl, CN, $NO_2$, COR, COOH, CONHR, $NR_2$, $NHCOCH_3$, $NHCOCF_3$, NHCOR, NHCONHR, NHCOOR, OCONHR, where R is hydrogen or alkyl; $NHCSCH_3$, alkylthio, alkylsulfinyl and alkylsulfonyl; the substituent(s) being preferably CN, $CF_3$, F or Cl. Typical examples of groups formed by the rings falling under the term "aliphatic, heteroaliphatic, aromatic or heteroaromatic ring" and the benzene ring, to which they are fused, are naphtalene, tetrahydronaphtalene, quinoline and benzofuran.

By the term "an aryl, heteroaryl, aliphatic or heteroaliphatic, 5-7-membered ring" in the definition of R11 is meant saturated or unsaturated ring having 5 to 7 ring members, 0 to 3 of which being a heteroatom selected from O, S and N, the other members being carbon atoms. Typical examples of R11 as an above defined ring are phenyl, pyridyl, cyclopentyl, furyl and tetrahydrofuryl. The ring may be substituted with 1-5 substituents selected from the group consisting of alkyl, halogen, (per)haloalkyl, CN, $NO_2$, COR, COOH, CONHR, $NR_2$, $NHCOCH_3$, $NHCOCF_3$, NHCOR, NHCONHR, NHCOOR, OCONHR, where R is hydrogen or alkyl; $NHCSCH_3$, alkylsulfinyl and alkylsulfonyl; the substitutuent(s) being preferably CN, $CF_3$, F or Cl.

Preferred compounds of formula (I) are those where z is 0 or 1.

Further preferred compounds of formula (I) are those wherein R2 is Cl, F, or CF$_3$.

Preferred are also those wherein R3 is nitro or cyano.

Further preferred compounds of formula (I) are those wherein one or both of R7 and R8 are independently selected from the group consisting of H, Cl, F, cyano, methoxy, and CF$_3$.

Especially preferred compounds of formula (I) are those wherein R2 is Cl, F, or CF$_3$; R3 is nitro or cyano and one or both of R7 and R8 are independently selected from the group consisting of H, Cl, F, cyano, methoxy, and CF3.

Preferred are also those wherein R11 is ethyl.

Preferred arylamides of the present invention are those of formula (I) where z is 0; R1 is H, halogen or (per)haloalkyl; R2 is halogen or (per)haloalkyl; R3 is CN, NO$_2$ or CONH$_2$; R4 and R5 are H or alkyl or R4 and R5 form together with the benzene ring a naphtalene ring; R6-R10 are H, (per)haloalkyl, halogen, NO$_2$, CN or CONH$_2$; X is SO$_2$ or O; and R11 is alkyl containing 2 to 5 carbon atoms, optionally substituted phenyl or furyl.

Another preferred group of compounds of formula (I) comprises those where z is 0; R1, R4 and R5 are H; R2 is selected from the group consisting of halogen and trifluoromethyl; R3 is selected from the group consisting of NO$_2$, CONH$_2$ and CN: R6, R7 and R10 are H; R8 and R9 are selected from the group consisting of H, halogen and trifluoromethyl, provided that at least one of R8 and R9 is other than H; X is selected from the group consisting of O and SO$_2$; and R11 is selected from the group consisting of alkyl containing up to 6 carbon atoms, phenyl optionally substituted with 1 or 2 halogenatoms or with 1 halogen atom and a further substituent selected from the group consisting of ON, NO$_2$, CONHR, NHCOR, NHSO$_2$R, where R is as defined in claim 1, and alkylsulfonyl; and furyl.

More preferred are the compounds of formula (I) where z is 0; R1, R4 and R5 are H; R2 is trifluoromethyl; R3 is CN; R6, R7 and R10 are H; R8 is trifluoromethyl; R9 is H; X is SO$_2$; and R11 is alkyl containing up to 4 carbon atoms; and the compounds of formula (I), where R1, R4 and R5 are H; R2 is chloro; R3 is CN: R6, R7 and R10 are H; R8 is trifluoromethyl; R9 is H; X is SO$_2$; and R11 is 4-fluorophenyl; and the compounds of formula (I) where R8 and R9 are both halogen or one of R8 and R9 is halogen and the other is selected from the group consisting of CN, NO$_2$, CONHR, NHCOR, NHSO$_2$R and alkylsulfonyl.

Preferred compounds are those of formula:

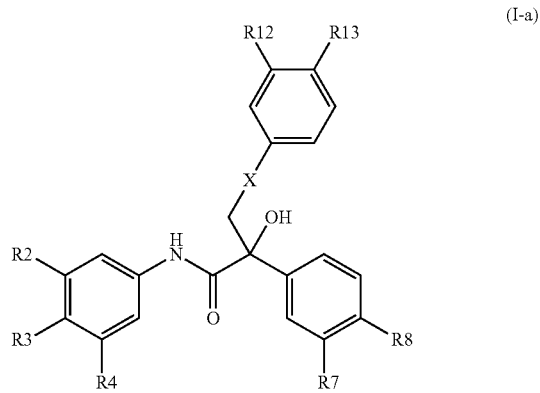

(I-a)

wherein R2, R3, R4, R7, and R8 are as defined earlier, and R12 and R13 are each independently selected from the group consisting of H, halo, cyano, and (per)haloalkyl.

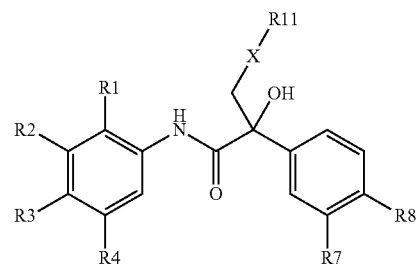

(I-b)

wherein R1, R2, R3, R4, R7, and R8 are as defined earlier, and R11 is as defined earlier, preferably C$_{1-4}$-alkyl;

and

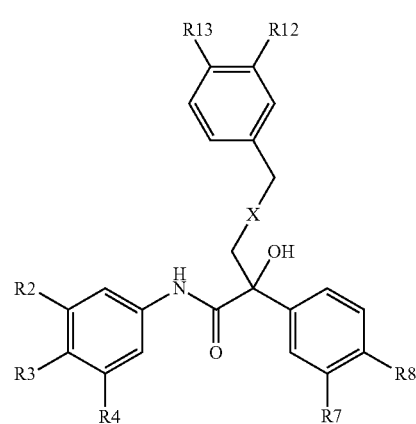

(I-c)

wherein R2, R3, R4, R7, and R8 are as defined earlier, and R12 and R13 are each independently selected from the group consisting of H, halo, cyano, and (per)haloalkyl.

and pharmaceutically acceptable salts thereof.

Preferred I-a, I-b, and I-c are those wherein R2 is Cl, F, or CF3.

Preferred I-a, I-b, and I-c are those wherein R3 is nitro or cyano.

Preferred I-a, I-b, and I-c are those wherein one or both of R7 and R8 are independently selected from the group consisting of H, Cl, F, cyano, methoxy, and CF$_3$.

Especially preferred I-a, I-b and I-c are those wherein R2 is Cl, F, or CF$_3$; R3 is nitro or cyano and one or both of R7 and R8 are independently selected from the group consisting of H, Cl, F, cyano, methoxy, and CF$_3$.

Preferred I-a and I-c are those wherein R12 and R13 are each independently selected from the group consisting of H, Cl, F, cyano and CF$_3$.

Preferred I-b are those wherein R11 is ethyl.

Examples of particularly preferred specific compounds are:

N-[4-cyano-3-(trifluoro-methyl)phenyl]-3-(ethanesulfonyl)-2-(4-fluorophenyl)-2-hydroxy-propanamide;

N-[4-cyano-3-(trifluoro-methyl)phenyl]-2-(4-fluorophenyl)-2-hydroxy-3-[(3-methylbutane)-sulfonyl]propanamide;

N-[4-cyano-3-(trifluoro-methyl)phenyl]-3-[(furan-2-yl-methane)sulfonyl]-2-hydroxy-2-[4-(trifluoro-methyl)phenyl]propanamide;

N-(3-chloro-4-cyano-phenyl)-3-[(4-fluoro-benzene)sulfonyl]-2-hydroxy-2-[4-(trifluoro-methyl)phenyl]propanamide;

N-(3-chloro-4-cyanophenyl)-2-(3,4-difluorophenyl)-3-(ethanesulfonyl)-2-hydroxy-propanamide;

N-(3-chloro-4-cyanophenyl)-3-[(3,4-difluorobenzene)sulfonyl]-2-(4-fluorophenyl)-2-hydroxypropanamide;

N-(3-chloro-4-cyanophenyl)-3-(ethanesulfonyl)-2-(4-fluorophenyl)-2-hydroxypropanamide;

N-(3-chloro-4-cyanophenyl)-3-[(3,4-difluorobenzene)sulfonyl]-2-hydroxy-2-[4-(trifluoromethyl)phenyl]propanamide;

N-(3-chloro-4-nitrophenyl)-3-[(4-fluorobenzene)sulfonyl]-2-hydroxy-2-[4-(trifluoromethyl)phenyl]propanamide;

N-(3-chloro-4-nitrophenyl)-3-[(3,4-difluorobenzene)sulfonyl]-2-hydroxy-2-[4-(trifluoromethyl)phenyl)]propanamide;

N-(4-nitro-3-trifluoromethylphenyl)-3-[(4-cyano-3-florobenzene)sulfonyl]-2-(4-fluorophenyl)-2-hydroxypropanamide;

N-(4-nitro-3-trifluoromethylphenyl)-3-[(4-cyano-3-fluorobenzene)sulfonyl]-2-(4-chlorophenyl)-2-hydroxypropanamide;

N-[4-cyano-3-(trifluoromethyl)phenyl]-3-(ethanesulfonyl)-2-[4-(trifuoromethyl)phenyl]-2-hydroxypropanamide;

N-(3-chloro-4-cyanophenyl)-3-[(4-chlorobenzene)sulfonyl]-2-(4-chlorophenyl)-2-hydroxypropanamide;

N-(3-chloro-4-nitrophenyl)-3-[(4-cyano,3-fluorobenzene)sulfonyl]-2-hydroxy-2-[4-(trifluoromethyl)phenyl]propanamide;

N-(3-chloro-4-cyanophenyl)-3-[(4(4-chlorobenzene)sulfonyl]-2-hydroxy-2-[4-(trifluoromethyl)phenyl]propanamide;

N-(4-cyano-3-(trifluoromethyl)phenyl)-3-[(4-fluorobenzene)sulfonyl]-2-hydroxy-2-[4-(trifluoromethyl)phenyl]propanamide;

N-(4-cyano-3-(trifluoromethyl)phenyl)-3-[(3,4-difluorobenzene)sulfonyl]-2-hydroxy-2-[3-fluoro-4-(methoxy)phenyl]propanamide;

N-(3-chloro-4-cyanophenyl)-3-(ethanesulfonyl)-2-hydroxy-2-[4-(chlorophenyl]propanamide;

N-(3-chloro-4-cyanophenyl)-2-((3-fluoro-4-methoxy)phenyl)-3-(ethanesulfonyl)-2-hydroxypropanamide;

N-[3-chloro-4-cyanophenyl]-3-{[(4-fluorophenyl)methane]sulfonyl}-2-hydroxy-2-[4-(chloro)phenyl]propanamide;

N-[3-chloro-4-cyanophenyl]-3-{[(4-chlorophenyl)methane]sulfonyl}-2-hydroxy-2-[4-(chloro)phenyl]propanamide;

N-[4-cyano-3-(trifluoromethyl)phenyl]-3-(ethanesulfonyl)-2-(4-chlorophenyl)-2-hydroxypropanamide;

N-(3-chloro-4-cyanophenyl)-3-{[(4-chlorophenyl)methane]sulfonyl}-2-hydroxy-2-[4-(trifluoromethyl)phenyl]propanamide;

N-(3-chloro-4-cyanophenyl)-2-(3-fluoro-4-methoxyphenyl)-3-{[(4-fluorophenyl)methane]sulfonyl}-2-hydroxypropanamide;

N-(3-chloro-4-cyanophenyl)-2-(3-fluoro-4-methoxyphenyl)-3-[(3-fluorobenzene)sulfonyl]-2-hydroxypropanamide;

N-[4-cyano-3-(trifluoromethyl)phenyl]-2-(3,4-difluorophenyl)-3-(ethanesulfonyl)-2-hydroxypropanamide;

N-(3-chloro-4-(cyanophenyl)-3-(ethanesulfonyl)-2-hydroxy-2-hydroxy-2-[3-(trifluoromethyl)phenyl]propanamide;

N-(3-chloro-4-(cyanophenyl)-3-{[(4-chlorophenyl)methane]sulfonyl}-2-(3-fluoro-4-methoxyphenyl)-2-hydroxypropanamide;

N-(3-chloro-4-(cyanophenyl)-3-[(3-fluorobenzene)sulfonyl]-2-hydroxy-2-[3-(trifluoromethyl)phenyl]propanamide;

N-(3-chloro-4-(cyanophenyl)-2-(3,4-difluorophenyl)-3-[(3-fluorobenzene)sulfonyl]-2-hydroxypropanamide;

N-[4-cyano-3-(trifluoromethyl)phenyl]-2-(3,4-difluorophenyl)-3-[(3-fluorobenzene)sulfonyl]-2-hydroxypropanamide;

N-(3-chloro-4-cyanophenyl)-3-{[(3-chlorophenyl)methane]sulfonyl}-2-hydroxy-2-[3-(trifluoromethyl)phenyl]propanamide;

N-(3-chloro-4-cyanophenyl)-3-{[(4-chlorophenyl)methane]sulfonyl}-2-hydroxy-2-[3-(trifluoromethyl)phenyl]propanamide;

N-(3-chloro-4-cyanophenyl)-2-(3,4-difluorophenyl)-3-[(4-fluorobenzene)sulfonyl]-2-hydroxypropanamide;

N-(3-chloro-4-cyanophenyl)-2-(3,4-difluorophenyl)-3-{[(4-fluorophenyl)methane]sulfonyl}-2-hydroxypropanamide;

N-(3-chloro-4-cyanophenyl)-3-{[(4-chlorophenyl)methane]sulfonyl}-2-(3,4-difluorophenyl)-2-hydroxypropanamide;

N-[4-cyano-3-(trifluoromethyl)phenyl]-2-(4-fluorophenyl)-2-hydroxy-3-(propane-1-sulfinyl)propanamide;

N-[4-cyano-3-(trifluoromethyl)phenyl]-2-(4-fluorophenyl)-2-hydroxy-3-(propane-1-sulfonyl)propanamide;

N-(3-chloro-4-cyano-2-fluorophenyl)-2-(3,4-difluorophenyl)-3-(ethanesulfonyl)-2-hydroxypropanamide;

and pharmaceutically acceptable salts thereof.

Pharmaceutically acceptable salts and their preparation are known in the art.

The arylamides of the invention may be prepared by methods described below. For example the compounds of formula (I), where X is O, SO or SO$_2$, may be prepared by reacting an epoxy compound of formula (5),

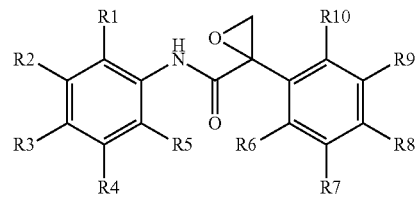

(5)

where R1-R10 are as defined above, with a compound of formula (II),

R11-(CR'R")$_2$—X'H        (II)

where R11, R', R" and z are as defined above and X' is O or S, to obtain a compound of formula (I), where X is O or S, and, if desired, oxidizing the obtained compound to obtain a compound of formula (I), where X is SO or SO$_2$. The process is preferably carried out via the following reaction steps:

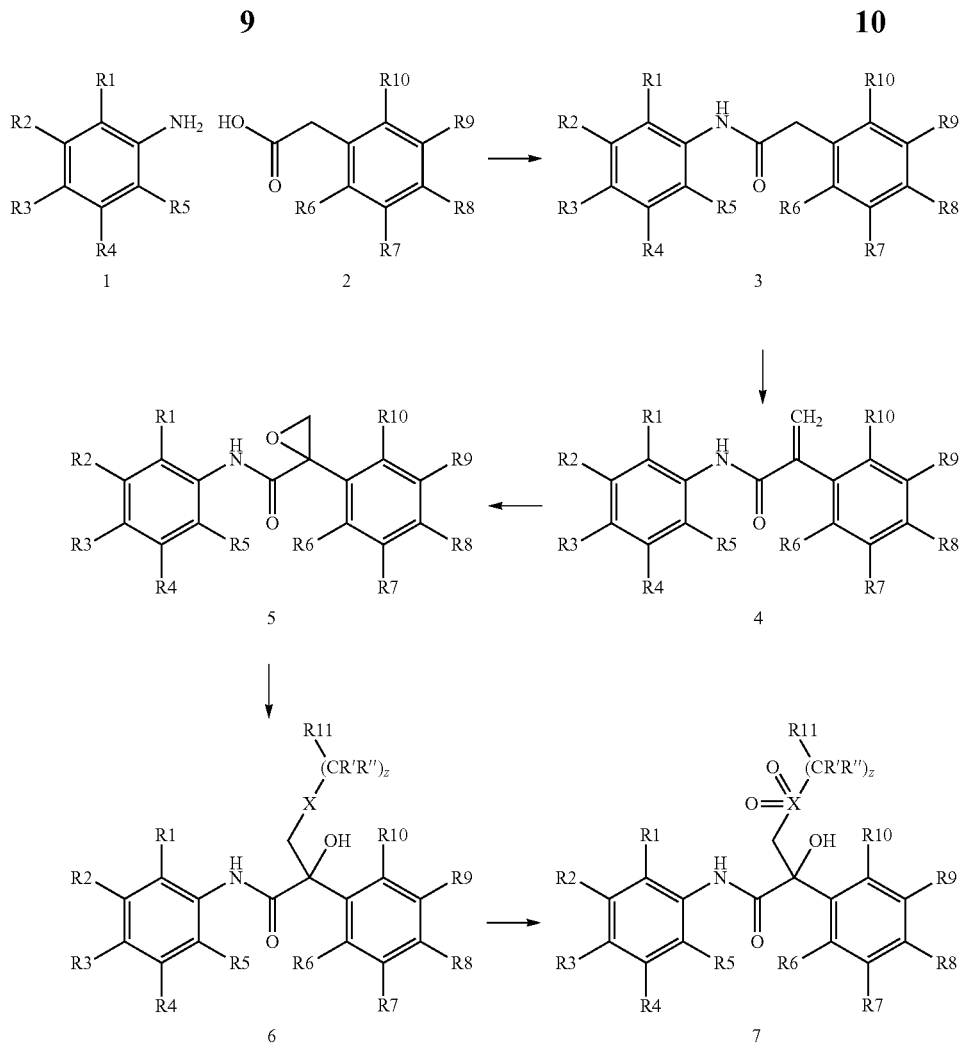

General Synthesis Procedure

The compounds of the present invention were synthesized using commercially available anilines, phenylacetic acids, thiols, phenols and amines as starting materials. 4-cyano-3-fluorothiophenol was synthesized from 4-cyano-3-fluorophenol using method described in WO 2008/008022. 4-cyano-3-chloro-2-fluoroaniline was synthesized from 3-chloro-2-fluoroaniline using method described in US 2005/0197359.

General Method for the Synthesis of the Intermediate (3)

A corresponding phenyl acetic acid (2) (3.89 mmol) was dissolved in dichloromethane and cooled in an ice bath to +5-0 degrees. 0.66 ml (2 equivalents) of oxalyl chloride was dropped in dichloromethane while keeping the temperature at +5-0 degrees. After addition was complete the ice bath was removed and the mixture was allowed to warm to room temperature (RT). After stirring for 4 hours, the mixture was cooled to 0 degree and the aniline (1) (3.89 mmol) was added in dimethylacetamide (10 ml). The resulting mixture was stirred at RT and monitored by TLC. After completion of the reaction, the mixture was poured in ice water and extracted with dichloromethane. The Organic phase was washed with water and dried over $Na_2SO_4$ and evaporated to give (3).

General Method for the Synthesis of the Intermediate (4)

1.7 mmol of (3), 0.075 g (1.8 equivalents) of paraformaldehyde and 0.412 g of $K_2CO_3$ was mixed in NMP (N-methyl pyrrolidone, 2 ml). The mixture was heated to 90 degrees and stirred for 3 hours. After cooling to RT 10 ml of water was added and the mixture was extracted with di-isopropyl ether (2×10 ml). The organic phase was washed with water (1×10 ml) and evaporated to give (4). The product was used for the synthesis of (5) without further purification.

General Method for the Synthesis of the Intermediate (5)

1.0 mmol of the intermediate (4) and 10 mg of 2,6-ditert-butyl-4-methylphenol was dissolved in $CH_2Cl_2$ (20 ml), 0.5 g (2 equivalents) of MCPBA was added. The mixture was stirred at RT overnight. The mixture was extracted with $Na_2CO_2$ and water. The organic phase was evaporated in vacuo to give the epoxide (5). Product was used without further purification for the synthesis of (6).

General Method for the Synthesis of (6)

To 3.0 (2 equivalents) mmol of $K_2CO_3$ in THF (5 ml), 2.2 mmol (1.5 equivalents) of a corresponding thiophenol or phenol was added in THF (7.5 ml) at 0° C. Mixture was stirred at 0° C. for 30 min. 1.5 mmol of the epoxide (5) in THF (7.5 ml) was added at 0° C. The resulting mixture was stirred at RT for 2 h, heated up to 50° C. and stirred for 12 h. After cooling the reaction was quenched with water. The resulting mixture was extracted with AcOEt. The organic phase was concentrated to get the crude material which was used for the synthesis of (7) without further purification. In case of phenols used in the reactions, the products were purified using flash chromatography.

General Method for the Synthesis of (7)

0.45 mmol of (6) was dissolved in $CH_2Cl_2$ (20 ml). MCPBA (0.90 mmol, 2 equivalents) was added and the mixture was stirred at RT. After completion of the reaction monitored by TLC reaction was quenched by saturated sodium sulphite solution in water and extracted with dichloromethane. The organic layer was washed with saturated sodium sulphite solution, dried over $Na_2SO_4$ and evaporated. Products were purified using flash chromatography.

Preparation of Sulfinyl Compounds

The sulfinyl compounds of the present invention were made from the corresponding intermediate (6) according to the procedure described by Bhise et al. in Synthetic communications, 2009, 39, 1516-1526 using sodium perborate trihydrate as an oxidation agent.

Preparation of Aromatic Amines from Epoxide (5)

The aromatic amines of the present invention were made from the corresponding intermediate (5) according to the procedure described by Dalton et al. in US 2006/0241180.

Preparation of Aliphatic Amines from Epoxide (5)

The aliphatic amines of the present invention were made from the corresponding intermediate (5) using similar method as described in case of thiols and phenols, but NaH was used as base in the reactions.

EXAMPLES

The compounds listed in Table 1 below were prepared using the synthesis procedure described above and illustrate the present invention.

TABLE 1

Names and 1H-NMR characteristics of Example molecules of the present invention

| Ex | Name | NMR |
|---|---|---|
| 1 | N-[4-cyano-3-(trifluoro-methyl)phenyl]-3-(ethanesulfonyl)-2-(4-fluorophenyl)-2-hydroxypropanamide | 1H NMR (CDCl3): 1.39 (3H, t, J = 7.4 Hz), 2.90-3.10 (2H, m), 3.55 (1H, d, J = 14.8 Hz), 4.14 (1H, d, J = 14.8 Hz), 5.88 (1H, bs), 7.11 (2H, m), 7.68 (2H, m), 7.78 (1H, m), 7.88 (1H, m), 8.06 (1H, m), 8.99 (1H, bs). |
| 2 | N-[4-cyano-3-(trifluoromethyl)phenyl]-2-(4-fluorophenyl)-2-hydroxy-3-[(3-methylbutane)-sulfonyl]propanamide | 1H NMR (CDCl3): 0.90 (6H, m), 1.62-1.71 (3H, m), 2.84-3.03 (2H, m), 3.57 (1H, d, J = 15.2 Hz), 4.12 (1H, d, J = 15.2 Hz), 7.10 (2H, m), 7.68 (2H, m), 7.77 (1H, m), 7.87 (1H, m), 8.09 (1H, m), 9.06 (1H, bs). |
| 3 | N-[4-cyano-3-(trifluoro-methyl)phenyl]-3-[(furan-2-ylmethane)sulfonyl]-2-hydroxy-2-[4-(trifluoromethyl)phenyl]propanamide | 1H NMR (CDCl3): 3.51 (1H, d, J = 15.2 Hz), 4.25 (1H, d, J = 15.2 Hz), 4.32 (1H, d, J = 15.2 Hz), 4.57 (1H, d, J = 15.2 Hz), 5.63 (1H, bs), 6.47 (1H, m), 6.63 (1H, m), 7.51 (1H, m), 7.67-7.91 (6H, m), 8.06 (1H, m), 8.95 (1H, bs). |
| 4 | N-(3-chloro-4-cyanophenyl)-3-[(4-fluorobenzene)sulfonyl]-2-hydroxy-2-[4-(trifluoromethyl)phenyl]propanamide | 1H NMR (CDCl3): 3.98 (1H, d, J = 14.8 Hz), 4.18 (1H, d, J = 14.8 Hz), 5.95 (1H, bs), 7.08 (2H, m), 7.40 (1H, m), 7.51 (2H, m), 7.59 (1H, m), 7.67 (4H, m), 7.80 (1H, m), 8.89 (1H, bs). |
| 5 | N-(3-chloro-4-cyanophenyl)-2-(3,4-difluorophenyl)-3-(ethanesulfonyl)-2-hydroxypropanamide | 1H NMR (CDCl3): 1.42 (3H, t, J = 7.2 Hz), 2.95-3.13 (2H, m), 3.48 (1H, d, J = 15.2 Hz), 4.15 (1H, d, J = 15.2 Hz), 5.93 (1H, bs), 7.22 (1H, m), 7.43 (1H, m), 7.47 (1H, m), 7.55 (1H, m), 7.61 (1H, m), 7.93 (1H, m), 8.83 (1H, bs). |
| 6 | N-(3-chloro-4-cyanophenyl)-3-[(3,4-difluorobenzene)sulfonyl]-2-(4-fluorophenyl)-2-hydroxypropanamide | 1H NMR (CDCl3): 3.92 (1H, d, J = 14.8 Hz), 4.20 (1H, d, J = 14.8 Hz), 6.98 (2H, m), 7.40 (1H, m), 7.43-7.54 (5H, m), 7.59 (1H, m), 7.80 (1H, m), 8.83 (1H, bs). |
| 7 | N-(3-chloro-4-cyanophenyl)-3-[(4-chlorobenzene)sulfonyl]-2-(4-fluorophenyl)-2-hydroxypropanamide | 1H NMR (CDCl3): 3.86 (1H, d, J = 14.9 Hz), 4.21 (1H, d, J = 14.9 Hz), 5.81 (1H, bs), 6.96 (2H, m), 7.37 (1H, m), 7.40 (2H, d, J = 8.6 Hz), 7.51 (2H, m), 7.59 (1H, m), 7.63 (2H, d, J = 8.6 Hz), 7.77 (1H, m), 8.83 (1H, bs). |
| 8 | N-(3-chloro-4-cyanophenyl)-3-(ethanesulfonyl)-2-(4-fluorophenyl)-2-hydroxypropanamide | 1H NMR (CDCl3): 1.39 (3H, t, J = 7.5 Hz), 2.85-3.05 (2H, m), 3.51 (1H, d, J = 15.2 Hz), 4.11 (1H, d, J = 15.2 Hz), 5.86 (1H, bs), 7.10 (2H, m), 7.44 (1H, m), 7.59 (1H, m), 7.66 (2H, m), 7.93 (1H, m), 8.81 (1H, bs). |
| 9 | N-(3-chloro-4-cyanophenyl)-3-(ethanesulfonyl)-2-hydroxy-2-[4-(trifluoromethy)phenyl]propanamide | 1H NMR (CDCl3): 1.41 (3H, t, J = 7.4 Hz), 2.95-3.11 (2H, m), 3.47 (1H, d, J = 15.0 Hz), 4.19 (1H, d, J = 15.0 Hz), 6.03 (1H, bs), 7.44 (1H, m), 7.59 (1H, m), 7.68 (2H, m), 7.82 (2H, m), 7.93 (1H, m), 8.87 (1H, bs). |
| 10 | N-(3-chloro-4-cyanophenyl)-3-[(3,4-difluorobenzene)sulfonyl]-2-hydroxy-2-[4-(trifluoromethyl)phenyl]propanamide | 1H NMR (CDCl3): 3.998 (1H, d, J = 15.1 Hz), 4.17 (1H, d, J = 15.1 Hz), 5.81 (1H, bs), 7.21 (1H, m), 7.35-7.49 (3H, m), 7.53 (2H, m), 7.59 (1H, m), 7.67 (2H, m), 7.79 (1H, m), 8.85 (1H, bs). |

TABLE 1-continued

Names and 1H-NMR characteristics of Example molecules of the present invention

| Ex | Name | NMR |
|---|---|---|
| 11 | N-(3-chloro-4-cyanophenyl)-3-[(4-cyano-3-fluorobenzene)sulfonyl]-2-hydroxy-2-[4-(trifluoromethyl)phenyl]propanamide | 1H NMR (CDCl3): 4.06 (1H, d, J = 15.2 Hz), 4.21 (1H, d, J = 15.2 Hz), 5.61 (1H, bs), 7.41 (1H, m), 7.45 (1H, m), 7.53 (2H, m), 7.60 (2H, m), 7.65 (2H, m), 7.72 (1H, m), 7.79 (1H, m), 8.79 (1H, bs). |
| 12 | N-(3-chloro-4-nitrophenyl)-3-[(4-fluorobenzene)sulfonyl]-2-hydroxy-2-[4-(trifluoromethyl)phenyl]propanamide | 1H NMR (CDCl3): 3.98 (1H, d, J = 15.0 Hz), 4.17 (1H, d, J = 15.0 Hz), 5.96 (1H, bs), 7.07 (2H, m), 7.44 (1H, m), 7.51 (2H, m), 7.66 (4H, m), 7.80 (1H, m), 7.93 (1H, m), 8.92 (1H, bs). |
| 13 | N-(3-chloro-4-nitrophenyl)-3-[(3,4-difluorobenzene)sulfonyl]-2-hydroxy-2-[4-(trifluoromethyl)phenyl]propanamide | 1H NMR (CDCl3): 4.02 (1H, d, J = 15.1 Hz), 4.18 (1H, d, J = 15.1 Hz), 5.82 (1H, bs), 7.21 (1H, m), 7.45 (3H, m), 7.53 (2H, m), 7.67 (2H, m), 7.81 (1H, m), 7.94 (1H, m), 8.89 (1H, bs). |
| 14 | N-(4-nitro-3-trifluoromethylphenyl)-3-[(4-cyano-3-fluorobenzene)sulfonyl]-2-(4-fluorophenyl)-2-hydroxypropanamide | 1H NMR (CDCl3): 4.03 (1H, d, J = 15.2 Hz), 4.22 (1H, d, J = 15.2 Hz), 5.51 (1H, bs), 6.98 (2H, m), 7.49 (3H, m), 7.62 (1H, m), 7.76 (1H, m), 7.86 (1H, m), 7.96 (2H, m), 8.94 (1H, bs). |
| 15 | N-(4-nitro-3-trifluoromethylphenyl)-3-[(3,4-difluorobenzene)sulfonyl]-2-(4-fluorophenyl)-2-hydroxypropanamide | 1H NMR (CDCl3): 3.93 (1H, d, J = 15.0 Hz), 4.19 (1H, d, J = 15.0 Hz), 5.75 (1H, bs), 6.98 (2H, m), 7.27 (1H, m), 7.51 (4H, m), 7.84 (1H, m), 7.95 (1H, m), 7.97 (1H, m), 9.00 (1H, bs). |
| 16 | N-(4-nitro-3-trifluoromethylphenyl)-3-[(4-cyano-3-fluorobenzene)sulfonyl]-2-(4-chloropheny)-2-hyroxypropanamide | 1H NMR (CDCl3): 4.07 (1H, d, J = 15.2 Hz), 4.17 (1H, d, J = 15.2 Hz), 5.52 (1H, bs), 7.24 (2H, m), 7.44 (3H, m), 7.58 (1H, m), 7.75 (1H, m), 7.86 (1H, m), 7.96 (2H, m), 8.93 (1H, bs). |
| 17 | N-[4-cyano-3-(trifluoromethyl)phenyl]-3-(ethanesulfonyl)-2-[4-(trifuoromethyl)phenyl]-2-hydroxypropanamide | 1H NMR (CDCl3): 1.41 (3H, t, J = 7.4 Hz), 2.90-3.08 (2H, m), 3.50 (1H, d, J = 15.1 Hz), 4.18 (1H, d, J = 15.1 Hz), 5.97 (1H, bs), 7.68 (2H, m), 7.75-7.90 (4H, m), 8.05 (1H, m), 8.96 (1H, bs). |
| 18 | N-(3-chloro-4-cyanophenyl)-3-[(4-chlorobenzene)sulfonyl]-2-(4-chlorophenyl)-2-hydroxypropanamide | 1H NMR (DMSO) 3.99 (1H, d, J = 14.7 Hz), 4.60 (1H, d, J = 14.7 Hz), 7.23 (1H, bs), 7.38 (2H, m), 7.54 (2H, m), 7.62 (2H, m), 7.84 (4H, m), 8.09 (1H, m), 10.43 (1H, bs). |
| 19 | N-(3-chloro-4-nitrophenyl)-3-[(4-cyano,3-fluorobenzene)sulfonyl]-2-hydroxy-2-[4-(trifluoromethyl)phenyl]propanamide | 1H NMR (CDCl3): 4.07 (1H, d, J = 15.2 Hz), 4.22 (1H, d, J = 15.2 Hz), 5.63 (1H, bs), 7.46 (2H, m), 7.53 (2H, m), 7.58 (1H, m), 7.66 (2H, m), 7.73 (1H, m), 7.80 (1H, m), 7.95 (1H, m), 8.83 (1H, bs). |
| 20 | N-(3-chloro-4-cyanophenyl)-3-[(4-chlorobenzene)sulfonyl]-2-hydroxy-2-[4-(trifluoromethyl)phenyl]propanamide | 1H NMR (CDCl3): 3.96 (1H, d, J = 15.0 Hz), 4.17 (1H, d, J = 15.0 Hz), 5.92 (1H, bs), 7.36 (3H, m), 7.50 (2H, m), 7.57 (3H, m), 7.65 (2H, m), 7.77 (1H, m), 8.85 (1H, bs). |
| 21 | N-(4-cyano-3-(trifluoromethyl)phenyl)-3-[(4-fluorobenzene)sulfonyl]-2-hydroxy-2-[4-(trifluoromethyl)phenyl]propanamide | 1H NMR (CDCl3): 3.98 (1H, d, J = 15.1 Hz), 4.18 (1H, d, J = 15.1 Hz), 5.98 (1H, bs), 7.07 (1H, m), 7.21 (1H, m), 7.50 (2H, m), 7.61 (1H, m), 7.67 (1H, m), 7.77 (2H, m), 7.91 (2H, m), 8.06 (1H, m), 8.99 (1H, bs). |
| 22 | N-(4-cyano-3-(trifluoromethyl)phenyl)-3-[(3,4-difluorobenzene)sulfonyl]-2-hydroxy-2-[3-fluoro-4-(methoxy)phenyl]propanamide | 1H NMR (CDCl3): 3.84 (3H, s), 3.95 (1H, d, J = 15.1 Hz), 4.12 (1H, d, J = 15.1 Hz), 5.67 (1H, bs), 6.83 (1H, m), 7.22 (2H, m), 7.28 (1H, m), 7.42 (1H, m), 7.52 (1H, m), 7.77 (2H, m), 7.96 (1H, m), 8.93 (1H, bs). |
| 23 | N-(3-chloro-4-cyanophenyl)-3-[(4-cyano,3-fluorobenzene)sulfonyl]-2-hydroxy-2-[3-fluoro-4-(methoxy)phenyl]propanamide | 1H NMR (CDCl3): 3.85 (3H, s), 3.94 (1H, d, J = 15.1 Hz), 4.13 (1H, d, J = 15.1 Hz), 5.76 (1H, bs), 7.18-7.60 (8H, m), 7.79 (1H, m), 8.80 (1H, bs). |
| 24 | N-(3-chloro-4-cyanophenyl)-3-(ethanesulfonyl)-2-hydroxy-2-[4-(chlorophenyl]propanamide | 1H NMR (CDCl3): 1.39 (3H, t, J = 7.4 Hz), 2.85-3.05 (2H, m), 3.50 (1H, d, J = 15.1 Hz), 4.11 (1H, d, J = 15.1 Hz), 5.87 (1H, bs), 7.38 (2H, m), 7.44 (1H, m), 7.60 (3H, m), 7.92 (1H, m), 8.80 (1H, bs). |
| 25 | N-(3-chloro-4-cyanophenyl)-2-((3-fluoro-4-methoxy)phenyl)-3-(ethanesulfonyl)-2-hydroxypropanamide | 1H NMR (CDCl3): 1.39 (3H, t, J = 6.9 Hz), 2.80-3.05 (2H, m), 3.50 (1H, d, J = 15.3 Hz), 3.88 (3H, s), 4.08 (1H, d, J = 15.3 Hz), 5.83 (1H, bs), 6.97 (1H, m), 7.30-7.63 (4H, m), 7.92 (1H, m), 8.80 (1H, bs). |

TABLE 1-continued

Names and 1H-NMR characteristics of Example molecules of the present invention

| Ex | Name | NMR |
|---|---|---|
| 26 | N-[3-chloro-4-cyanophenyl]-3-{[(4-fluorophenyl)methane]sulfonyl}-2-hydroxy-2-[4-(chloro)phenyl]propanamide | 1H NMR (CDCl3): 3.20 (1H, d, J = 15.3 Hz), 4.13 (1H, d, J = 15.3 Hz), 4.19 (1H, d, J = 14.0 Hz), 4.42 (1H, d, J = 14.0 Hz), 5.67 (1H, bs), 7.12 (2H, m), 7.37 (2H, m), 7.49 (4H, m), 7.55 (2H, m), 7.61 (1H, m), 8.75 (1H, bs). |
| 27 | N-[3-chloro-4-cyanophenyl]-3-{[(4-chlorophenyl)methane]sulfonyl}-2-hydroxy-2-[4-(chloro)phenyl]propanamide | 1H NMR (CDCl3): 3.20 (1H, d, J = 15.3 Hz), 4.13 (1H, d, J = 15.3 Hz), 4.19 (1H, d, J = 13.8 Hz), 4.43 (1H, d, J = 13.8 Hz), 5.65 (1H, bs), 7.37 (4H, m), 7.46 (3H, m), 7.54 (2H, m), 7.61 (1H, m), 7.96 (1H, m), 8.74 (1H, bs). |
| 28 | N-[4-cyano-3-(trifluoromethyl)phenyl]-3-(ethanesulfonyl)-2-(4-chlorophenyl)-2-hydroxypropanamide | 1H NMR (CDCl3): 1.39 (3H, t, J = 7.4 Hz), 2.89-3.10 (2H, m), 3.52 (1H, d, J = 15.1 Hz), 4.11 (1H, d, J = 15.1 Hz), 5.89 (1H, bs), 7.39 (2H, m), 7.62 (2H, m), 7.77 (1H, m), 7.85 (1H, m), 8.04 (1H, m), 8.93 (1H, bs). |
| 29 | 2-(4-chlorophenyl)-N-[4-cyano-3-(trifluoromethyl)phenyl]-3-(3,4-difluorophenoxy)-2-hydroxypropanamide | 1H NMR (CDCl3): 3.90 (1H, s), 4.01 (1H, d, J = 6.8 Hz), 4.81 (1H, d, J = 6.8 Hz), 6.60 (1H, m), 6.76 (1H, m), 7.07 (1H, m), 7.39 (2H, m), 7.66 (2H, m), 7.78 (1H, m), 7.92 (1H, m), 8.06 (1H, m), 9.02 (1H, bs). |
| 30 | N-(3-chloro-4-cyanophenyl)-3-{[(4-fluorophenyl)methane]sulfonyl}-2-hydroxy-2-[4-(trifluoromethyl)phenyl]propanamide | 1H NMR (CDCl3): 3.18 (1H, d, J = 15.4 Hz), 4.18 (1H, d, J = 15.4 Hz), 4.22 (1H, d, J = 13.9 Hz), 4.48 (1H, d, J = 13.9 Hz), 5.71 (1H, bs), 7.38-7.50 (5H, m), 7.60-7.77 (5H, m), 7.96 (1H, m), 8.76 (1H, bs). |
| 31 | N-(3-chloro-cyanophenyl)-3-{[(4-chlorophenyl)methane]sulfonyl}-2-hydroxy-2-[4-(trifluoromethyl)phenyl]propanamide | 1H NMR (CDCl3): 3.19 (1H, d, J = 15.6 Hz), 4.18 (1H, d, J = 15.6 Hz), 4.23 (1H, d, J = 14.0 Hz), 4.48 (1H, d, J = 14.0 Hz), 5.74 (1H, bs), 7.13 (3H, m), 7.38-7.77 (7H, m), 7.96 (1H, m), 8.77 (1H, bs). |
| 32 | N-(3-chloro-4-cyanophenyl)-2-(3-fluoro-4-methoxyphenyl)-3-{[(4-fluorophenyl)methane]sulfonyl}-2-hydroxypropanamide | 1H NMR (CDCl3): 3.22 (1H, d, J = 15.1 Hz), 3.87 (3H, s), 4.11 (1H, d, J = 15.1 Hz), 4.18 (1H, d, J = 14.0 Hz), 4.41 (1H, d, J = 14.0 Hz), 5.64 (1H, bs), 6.96 (1H, m), 7.12 (2H, m), 7.28 (1H, m), 7.36 (1H, m), 7.46-7.55 (3H, m), 7.61 (1H, m), 7.96 (1H, m), 8.75 (1H, bs). |
| 33 | N-(3-chloro-4-cyanophenyl)-2-(3-fluoro-4-methoxyphenyl)-3-[(3-fluorobenzene)sulfonyl]-2-hydroxypropanamide | 1H NMR (CDCl3): 3.84 (3H, s), 3.95 (1H, d, J = 15.0 Hz), 4.12 (1H, d, J = 15.0 Hz), 5.74 (1H, bs), 7.22-7.59 (9H, m), 7.79 (1H, m), 8.81 (1H, bs). |
| 34 | N-[4-cyano-3-(trifluoromethyl)phenyl]-2-(3,4-difluorophenyl)-3-(ethanesulfonyl)-2-hydroxypropanamide | 1H NMR (CDCl3): 1.41 (3H, t, J = 7.4 Hz), 2.90-3.07 (2H, m), 3.47 (1H, d, J = 14.9 Hz), 4.13 (1H, d, J = 14.9 Hz), 5.95 (1H, bs), 7.22 (1H, m), 7.42 (1H, m), 7.55 (1H, m), 7.79 (1H, m), 7.88 (1H, m), 8.05 (1H, m), 8.93 (1H, bs). |
| 35 | N-(3-chloro-4-cyanophenyl)-3-(ethanesulfonyl)-2-hydroxy-2-[3-(trifluoromethyl)phenyl]propanamide | 1H NMR (CDCl3): 1.41 (3H, t, J = 7.4 Hz), 2.90-3.15 (2H, m), 3.48 (1H, d, J = 15.0 Hz), 4.18 (1H, d, J = 15.0 Hz), 5.97 (1H, bs), 7.46 (1H, m), 7.55 (1H, m), 7.60 (1H, m), 7.64 (1H, m), 7.86 (1H, m), 7.93 (1H, m), 7.98 (1H, m), 8.84 (1H, bs). |
| 36 | N-(3-chloro-4-cyanophenyl)-3-{[(4-chlorophenyl)methane]sulfonyl}-2-(3-fluoro-4-methoxyphenyl)-2-hydroxypropanamide | 1H NMR (CDCl3): 3.22 (1H, d, J = 15.3 Hz), 3.87 (3H, s), 4.10 (1H, d, J = 15.3 Hz), 4.16 (1H, d, J = 13.9 Hz), 4.41 (1H, d, J = 13.9 Hz), 5.61 (1H, bs), 6.96 (1H, m), 7.29 (1H, m), 7.30-7.51 (6H, m), 7.61 (1H, m), 7.96 (1H, m), 8.74 (1H, bs). |
| 37 | N-(3-chloro-4-cyanophenyl)-3-[(3-fluorobenzene)sulfonyl]-2-hydroxy-2-[3-(trifluoromethyl)phenyl]propanamide | 1H NMR (CDCl3): 3.98 (1H, d, J = 15.0 Hz), 4.19 (1H, d, J = 15.0 Hz), 5.95 (1H, bs), 7.27 (2H, m), 7.35-7.45 (3H, m), 7.52 (2H, m), 7.58 (1H, m), 7.73 (1H, m), 7.80 (1H, m), 7.81 (1H, m), 8.89 (1H, bs). |
| 38 | N-(3-chloro-4-cyanophenyl)-2-(3,4-difluorophenyl)-3-[(3-fluorobenzene)sulfonyl]-2-hydroxypropanamide | 1H NMR (CDCl3): 3.88 (1H, d, J = 14.9 Hz), 4.16 (1H, d, J = 14.9 Hz), 5.88 (1H, bs), 7.05 (1H, m), 7.25-7.60 (8H, m), 7.78 (1H, m), 8.84 (1H, bs). |
| 39 | N-[4-cyano-3-(trifluoromethyl)phenyl]-2-(3,4-difluorophenyl)-3-[(3-fluorobenzene)sulfonyl]-2-hydroxypropanamide | 1H NMR (CDCl3): 3.87 (1H, d, J = 14.3 Hz), 4.19 (1H, d, J = 14.8 Hz), 5.90 (1H, bs), 7.07 (1H, m), 7.27-7.52 (6H, m), 7.55 (1H, m), 7.76 (1H, m), 7.95 (1H, m), 8.99 (1H, bs). |

TABLE 1-continued

Names and 1H-NMR characteristics of Example molecules of the present invention

| Ex | Name | NMR |
|---|---|---|
| 40 | N-(3-chloro-4-cyanophenyl)-3-{[(4-fluorophenyl)methane]sulfonyl}-2-hydroxy-2-[3-(trifluoromethyl)phenyl]propanamide | 1H NMR (CDCl3): 3.21 (1H, d, J = 15.2 Hz), 4.19 (1H, d, J = 15.2 Hz), 4.22 (1H, d, J = 14.0 Hz), 4.44 (1H, d, J = 14.0 Hz), 5.77 (1H, bs), 7.12 (2H, m), 7.48 (4H, m), 7.61 (2H, m), 7.79 (1H, m), 7.98 (2H, m), 8.81 (1H, bs). |
| 41 | N-(3-chloro-4-cyanophenyl)-3-{[(4-chlorophenyl)methane]sulfonyl}-2-hydroxy-2-[3-(trifluoromethyl)phenyl]propanamide | 1H NMR (CDCl3): 3.21 (1H, d, J = 15.2 Hz), 4.19 (1H, d, J = 15.2 Hz), 4.22 (1H, d, J = 13.9 Hz), 4.44 (1H, d, J = 13.9 Hz), 5.75 (1H, bs), 7.36-7.57 (6H, m), 7.63 (2H, m), 7.78 (1H, m), 7.93 (1H, m), 7.97 (1H, m), 8.80 (1H, bs). |
| 42 | N-(3-chloro-4-cyanophenyl)-2-(3,4-difluorophenyl)-3-[(4-fluorobenzene)sulfonyl]-2-hydroxypropanamide | 1H NMR (CDCl3): 3.84 (1H, d, J = 14.8 Hz), 4.20 (1H, d, J = 14.8 Hz), 5.96 (1H, bs), 7.08 (1H, m), 7.17 (2H, m), 7.31 (1H, m), 7.42 (2H, m), 7.61 (1H, m), 7.77 (2H, m), 7.81 (1H, m), 8.88 (1H, bs). |
| 43 | N-(3-chloro-4-cyanophenyl)-2-(3,4-difluorophenyl)-3-{[(4-fluorophenyl)methane]sulfonyl}-2-hydroxypropanamide | 1H NMR (CDCl3): 3.17 (1H, d, J = 15.5 Hz), 4.14 (1H, d, J = 15.5 Hz), 4.21 (1H, d, J = 14.0 Hz), 4.45 (1H, d, J = 14.0 Hz), 5.73 (1H, bs), 7.13 (2H, m), 7.20 (2H, m), 7.34 (1H, m), 7.49 (3H, m), 7.62 (1H, m), 7.96 (1H, m), 8.76 (1H, bs). |
| 44 | N-(3-chloro-4-cyanophenyl)-3-{[(4-chlorophenyl)methane]sulfonyl}-2-(3,4-difluorophenyl)-2-hydroxypropanamide | 1H NMR (CDCl3): 3.16 (1H, d, J = 15.2 Hz), 4.13 (1H, d, J = 15.2 Hz), 4.20 (1H, d, J = 13.9 Hz), 4.45 (1H, d, J = 13.9 Hz), 5.70 (1H, bs), 7.18 (2H, m), 7.34 (1H, m), 7.41 (2H, m), 7.48 (3H, m), 7.63 (1H, m), 7.97 (1H, m), 8.75 (1H, bs). |
| 45 | N-[4-cyano-3-(trifluoromethyl)phenyl]-2-(4-fluorophenyl)-2-hydroxy-3-(propane-1-sulfinyl)propanamide | Mixture of two diastereomers 1H NMR (CDCl3): 1.07 (3H, m), 1.80 (2H, m), 2.70-2.95 (2H, m), 2.99/3.29 (1H, d/d, J = 12.8/13.2 Hz), 3.71/3.72 (1H, d/d, J = 12.8/13.2 Hz), 6.80/6.94 (1H, bs/bs), 7.10 (2H, m), 7.70 (2H, m), 7.77 (1H, m), 7.85 (1H, m), 8.07/8.13 (1H, m/m), 9.09/9.19 (1H, bs/bs). |
| 46 | N-[4-cyano-3-(trifluoromethyl)phenyl]-2-(4-fluorophenyl)-2-hydroxy-3-(propane-1-sulfonyl)propanamide | 1H NMR (CDCl3): 1.03 (3H, t, J = 7.4 Hz), 1.86 (2H, m), 2.70-3.00 (2H, m), 3.56 (1H, d, J = 15.0 Hz), 4.08 (1H, d, J = 15.0 Hz), 5.89 (1H, bs), 7.11 (2H, m), 7.67 (2H, m), 7.78 (1H, m), 7.86 (1H, m), 8.05 (1H, m), 8.95 (1H, bs), |
| 47 | N-(3-chloro-4-cyanophenyl)-2-hydroxy-3-(morpholin-4-yl)-2-[4-(trifluoromethyl)phenyl]propanamide | 1H NMR (CDCl3): 2.48 (2H, m), 2.57 (2H, m), 2.67 (1H, d, J = 13.1 Hz), 3.62 (1H, d, J = 13.1 Hz), 3.67 (4H, m), 5.95 (1H, bs), 7.47 (1H, m), 7.57 (1H, m), 7.61 (2H, m), 7.80 (2H, m), 7.91 (1H, m), 9.14 (1H, bs). |
| 48 | N-(3-chloro-4-cyanophenyl)-3-(diethylamino)-2-hydroxy-2-[4-(trifluoromethyl)phenyl]propanamide | 1H NMR (CDCl3): 0.98 (6H, m), 2.55 (4H, m), 2.65 (1H, d, J = 13.4 Hz), 3.70 (1H, d, J = 13.4 Hz), 7.46 (1H, m), 7.57 (1H, m), 7.60 (2H, m), 7.81 (2H, m), 7.92 (1H, m), 9.24 (1H, bs). |
| 49 | N-(3-chloro-4-cyanophenyl)-3-[(4-fluorophenyl)amino]-2-hydroxy-2-[4-(trifluoromethyl)phenyl]propanamide | 1H NMR (CDCl3): 3.41 (1H, d, J = 13.3 Hz), 4.21 (1H, d, J = 13.3 Hz), 4.46 (1H, bs), 6.69 (2H, m), 6.90 (2H, m), 7.47 (1H, m), 7.58 (1H, m), 7.67 (2H, m), 7.85 (2H, m), 7.94 (1H, m), 8.92 (1H, bs). |
| 50 | N-(3-chloro-4-cyano-2-fluorophenyl)-2-(3,4-difluorophenyl)-3-(ethanesulfonyl)-2-hydroxypropanamide | 1H NMR (CDCl3): 1.40 (3H, t, J = 7.1 Hz), 2.99 (2H, m), 3.49 (1H, d, J = 14.9 Hz), 4.12 (1H, d, J = 14.9 Hz), 5.93 (1H, bs), 7.20 (1H, m), 7.45 (2H, m), 7.55 (1H, m), 8.40, 9.12 (1H, bs). |

General Description of the Pharmacological Properties of the Compounds of the Present Invention The arylamide derivatives of the present invention show high antagonistic activity in AR. Antagonistic activity in AR refers to potency of the compound to compete and/or inhibit the activity of natural AR ligands such as dihydrotestosterone (DHT) and testosterone. The present invention provides compounds having antagonistic activity in AR to compete and/or inhibit the activity of non-natural AR ligands, such as synthetic androgens or anti-androgens used as medicaments (but which may exert deleterious side-effects).

Further, the present invention provides compounds that demonstrate potent anti-androgen activity in a dose-dependent manner. A major disadvantage of bicalutamide is incomplete AR antagonism. In the case of bicalutamide, increasing concentrations do not provide significant extra benefit (see Table 2). More potent anti-androgens than bicalutamide may be needed to treat advanced stage of PCa characterized by elevation of AR levels, thus there is a need for potent anti-androgens that can compensate for the elevated AR levels in a dose-dependent manner. The present invention provides compounds that exert minimal agonistic effects in AR.

The compounds of the present invention can be used to treat AR-related diseases, such as BPH and PCa. The compounds can also be used to treat CRPC. Further, the compounds can be used in combination with other anti-androgen treatments.

The compounds of the present invention do not gain agonistic activity in CRPC related mutations. By CRPC related mutations, all mutations that affect the development, progression or severity of the disease are referred. The CRPC related mutation may have resulted from androgen deprivation-induced enrichment of prostate cancer cells harboring the said mutation. For instance tryptophan 741 to leucine or to cysteine mutation and also threonine 877 to alanine mutation are referred.

The compounds of the present invention retain their antagonistic activities when AR levels are elevated, The following tests and results are provided as to demonstrate the present invention in an illustrative way and should not be considered as limiting in the scope of invention. Further, the concentrations of the compounds in the assays are exemplary and should not be taken as limiting. A person skilled in the art may define pharmaceutically relevant concentrations with methods known in the art.

Experiments

To elucidate the potency of the compounds of the present invention to function as anti-androgens and to demonstrate that the compounds of the present invention retain their antagonistic activity in conditions known to confer agonistic activities in the first-line anti-androgen medications in clinical use (such as flutamide or bicalutamide, BIC) a series of in vitro studies was designed. These studies were based on measuring AR transactivation using a reporter gene assay, which is a well-established, golden standard assay in AR research. Depending on the presence or absence of natural AR ligand such as testosterone, this reporter gene assay can be used to determine both antagonistic and agonistic activity of the compounds. BIC was used as a reference compound in all studies representing currently available standard anti-androgen treatment.

AR Transactivation Assay

COS-1 (American Type Culture Collection) were cultured in DMEM supplemented with 10% FBS, penicillin (6.25 U/ml) and streptomycin (6.25 µg/ml) and seeded onto 48-well plates (50 000 cells/well) one day before transfection. Transfection media containing 2.5% charcoal-stripped FBS in DMEM was changed on cells 4 h prior to transfection. Cells were transfected with 50 ng of reporter gene plasmid (pPB-286/+32-LUC; PB, probasin promoter), 5 ng of AR expression plasmid (pSG5-hAR), and 5 ng of pCMVβ (an internal, beta-galactosidase control for transfection efficiency and cell growth) using TransIT-LT1 reagent (Mirus Bio Corporation) according to the manufacturer's instructions. One day after transfection, triplicate wells received either (i) vehicle (EtOH-DMSO), (ii) 50 nM testosterone (reference agonist, from Makor or Steraloids Inc.), (iii) increasing concentrations of BIC (reference antagonist) or (iv) compound of the present invention alone (to test for agonism) or (v) increasing concentrations of BIC (reference antagonist) or (vi) compound of the present invention together with the reference agonist in a competitive setting (50 nM; to test for antagonism of testosterone induced AR transcription). After 18 h, reporter gene activities (LUC and beta-galactosidase) were determined according to standard methods. The data are expressed as relative LUC activity (luciferase light units divided by beta-galactosidase $A420_{nm}$ to control for transfection efficiency) of a given compound in relation to the activity of a reference test item (=100%).

Agonism in WT AR

Agonism in WT AR of compounds of the present invention was measured in AR transactivation assay in COS-1 cells by exposing the transfected cells to test compounds alone as described above. Testosterone was used as a reference agonist, Relative LUC activity representing the level of AR activation was measured. The response obtained by the reference agonist was set as 100%. The compounds of the present invention did not show agonism in WT AR.

Antagonism in Wild Type (WT) AR

Antagonism in WT AR of compounds of the present invention was measured in AR transctivation assay in COS-1 cells in competitive setting using testosterone as a reference agonist as described above. Known anti-androgen BIC was used as a reference antagonist. Relative LUC activity representing AR-dependent transcription obtained by exposure to testosterone alone was set to 100%. The compounds of the present invention were efficient antagonists in WT AR (Table 2).

TABLE 2

Antagonism in WT AR

| | Relative LUC activity (%) indicating residual androgen activity in relation to testosterone (100%) | |
|---|---|---|
| Ex | 1 microM | 10 microM |
| 1 | 24 | 9 |
| 2 | 12 | 3 |
| 3 | 17 | 3 |
| 4 | 21 | 1 |
| 5 | 33 | 7 |
| 6 | 7 | 5 |
| 10 | 23 | 6 |
| 17 | 18 | 3 |
| 18 | 7 | 1 |
| 19 | 11 | 1 |
| 21 | 24 | 1 |
| 22 | 9 | 3 |
| 25 | 22 | 6 |
| 27 | 14 | 1 |
| 32 | 24 | 2 |
| 33 | 5 | 1 |
| 35 | 18 | 6 |
| 39 | 14 | 2 |
| 40 | 22 | 2 |
| BIC | 20 | 12 |

One of the major limitations in the use of currently available anti-androgens, such as flutamide and BIC, is the antagonist-agonist conversion observed in mutated AR.

Agonism in W741L Mutant AR

Agonism in W741L AR of compounds of the present invention was measured in AR transactivation assay in COS-1 cells as described above except that AR expression vector harboring the W741L mutation was used instead of the WT AR. The transfected cells were exposed to test compounds alone. BIC was used as a reference compound. As reported in literature, BIC functions as an agonist in this mutant AR variant and the relative LUC activity representing AR-dependent transcription induced by BIC was set to 100%. The compounds of the present invention did not show agonism in W741 L AR (Table 3).

Agonism in T877A Mutant AR

Agonism in T877A AR of compounds of the present invention was measured in AR transactivation assay in COS-1 cells as described above except that AR expression vector harboring the T877A mutation was used. The transfected cells were exposed to test compounds alone. Testosterone was used as reference agonist, and its' relative LUC activity representing AR-dependent transcription was set to 100%. The compounds of the present invention did not show agonism in T877A AR (Table 3).

TABLE 3

Agonism in W741L and T877A mutant AR

| Ex | Relative LUC activity (%) in W741L AR in relation to BIC (100%) 10 microM | Relative LUC activity (%) in T877A AR in relation to testosterone (100%) 10 microM |
|---|---|---|
| 1 | 12 | 14 |
| 3 | 4 | 3 |
| 4 | 8 | 1 |
| 5 | 18 | 9 |
| 10 | 3 | 1 |
| 18 | 27 | 6 |
| 19 | 9 | 2 |
| 21 | 3 | 4 |
| 25 | 9 | 9 |
| 27 | 6 | 1 |
| 32 | 3 | 2 |
| 40 | 2 | 1 |
| BIC | 100 | 14 |

Antagonism in T877A Mutant AR

To confirm that the compounds of the present invention retain antagonism in mutant AR, the compounds of the present invention were subjected to AR transactivation assay in a competitive setting together with testosterone as described above except that AR expression vector harboring the T877A mutation was used. Relative LUC activity representing AR-dependent transcription obtained by exposure to testosterone alone was set to 100%. The compounds of present invention retained their antagonistic properties in T877A mutant AR.

Gene Expression in VCaP Cells

Quantitative RT-PCR was used to study the ability of the compounds of the present invention to inhibit AR target gene expression. VCaP cells were seeded onto 12-well plates ($3 \times 10^5$ cells/well) and triplicate wells were treated with either (I) vehicle (EtOH-DMSO), or (ii) 1 nM R1881 (reference agonist, Perkin-Elmer), or (iii) increasing concentrations of BIC (reference antagonist), or (iv) the test compound together with the reference agonist (1 nM) (all final concentrations). After 18 h, total RNA was extracted using TRI-zol® Reagent (Invitrogen Life Technologies) and converted to cDNA using Transcriptor First Strand cDNA synthesis Kit (Roche Diagnostics GmbH) following manufacturer's instructions, cDNA was used as a template in RT-qPCR, which was carried out using Mx3000P Real-Time PCR System (Stratagene), FastStart SYBR Green Master Mix (Roche) and specific primers for AR target genes, PSA, TMPRSS2 and FKBP51. Analyzed GAPDH mRNA levels were used to normalize the amounts of total RNA between the samples. Fold changes (ligand inductions) were calculated using the formula $2^{-(\Delta\Delta Ct)}$, where $\Delta\Delta Ct$ is $\Delta Ct_{(ligand)} - \Delta Ct_{(EtOH-DMSO)}$, $\Delta Ct$ was $Ct_{(gene\ X)} - Ct_{(GAPDH)}$ and Ct was the cycle at which the threshold was crossed. Gene expression data were expressed as relative mRNA level (mRNA level of the gene of interest divided by mRNA level of GAPDH) of each gene for a given compound. The compounds of the present invention efficiently silenced AR target gene expression in VCaP cells.

LNCaP Proliferation Assay

The ability of the compounds of the present invention to inhibit prostate cancer cell growth was studied in androgen sensitive human prostate adenocarcinoma cell line, LNCaP. The cells were seeded onto 96-well plates (5000 cells/well) and cultured for 72 h. The triplicate wells were treated either with (i) vehicle (EtOH-DMSO) or (ii) 0.1 nM R1881 (reference agonist, Perkin-Elmer), or (iii) increasing concentrations of BIC (the reference antagonist), or (iv) the test compound together with the reference agonist (0.1 nM) (all final concentrations) for 5 days. LNCaP cell proliferation was measured on day 0, day 1, day 3 and day 5 using Promega's Cell Titer 96® $AQ_{ueous}$ One Solution Cell Proliferation Assay kit according to manufacturer's instructions. 20 µl of the Cell Titer reagent was added into 100 µl of cell culture medium in each well and the cells were allowed to grow for one hour in the incubator. The culture medium was transferred into the wells of the measuring plate and the absorbance at 492 nm was recorded. The compounds of the present invention inhibited LNCaP proliferation.

AR Binding Assay

The ability of the test compounds to bind to AR was measured by relative binding inhibition (RBI), i.e. their ability to displace $^3$H-labeled synthetic agonist R1881 from AR expressed in COS-1 cells. COS-1 cells were transfected as above for reporter gene assays, except for 24-well plates (100 000 cells/well) and 50 ng of pSG5-AR (in the absence of other plasmids) were used. Forty hours after the transfection, the medium was removed, the wells were washed once with PBS and 0.5 ml of DMEM (without serum) and 5 microl of [$^3$H] R1881 (Perkin Elmer; 72 Ci/mmol, 1 microCi/microl) that was diluted 1+129 with DMEM were added (yielding final concentration of 1 nM [$^3$H]R1881 in the well). The triplicate wells received: (i) no 'cold' ligand (EtOH+DMEM), (ii) 20 nM 'cold' R1881, (iii) 200 nM 'cold' R1881, (iv) 'cold' BIC or (v) 'cold' test compound at 200 nM, 2000 nM, and 10000 nM concentration. After incubation for 2 h at 37° C. the radioactivity was measured. The relative $^3$H activity (cpm) of R1881 was set to 100%, and the relative binding inhibition was counted for the test compounds. The compounds of the present invention showed concentration dependent binding affinity to AR.

The compounds of the present invention exhibit little or no agonistic activity to androgen receptor. Because these compounds are potent AR antagonists they can be used not only to treat prostate cancer but to treat other androgen receptor related conditions and diseases such as benign prostate hyperplasia, hair loss, acne, hirsutism, male hypersexuality or polycystic ovarian syndrome.

As it pertains to the treatment of cancer, the compounds of this invention are most preferably used alone or in combination with anti-androgenic cancer treatments. Such compounds may also be combined with agents which suppress the production of circulating testosterone such as LHRH agonists or antagonists or with surgical castration.

The present invention also contemplates use of an antiestrogen and/or aromatase inhibitor in combination with a compound of the present invention, for example, to assist in mitigating side effects associated with anti-androgen therapy such as gynecomastia.

AR belongs to the superfamily of nuclear receptors and the compounds of the present invention can also be used as scaffolds for drug design for other nuclear hormone receptors such as estrogen receptor or peroxisome proliferator-activated receptor. Therefore, the compounds of the present invention can also be further optimized to be used in treating other conditions and diseases such as ovarian cancer, breast cancer, diabetes, cardiac diseases, metabolism related diseases of the periphery and central nervous system in which nuclear receptors play a role.

The compounds of the invention may be administered by intravenous injection, by injection into tissue, intraperitoneally, orally, or nasally. The composition may have a form selected from the group consisting of a solution, dispersion, suspension, powder, capsule, tablet, pill, controlled release capsule, controlled release tablet, and controlled release pill.

The invention claimed is:

1. An arylamide derivative having formula (I)

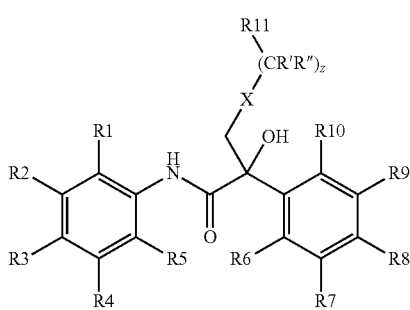

(I)

or pharmaceutically acceptable salts thereof or stereoisomers of Formula I;
where
R' and R" are each independently selected from the group consisting of H and alkyl;
z is an integer 0 to 3;
R1 is selected from the group consisting of H, halogen, (per)haloalkyl, hydroxy and $(CH_2)_nCHO$, where n is an integer 0-6;
R2 is selected from the group consisting of H, alkyl, halogen, trifluoromethyl, (halo)alkyl, hydroxy and $(CH_2)_nCHO$, where n is an integer 0-6;
R3 is selected from the group consisting of $NO_2$, CN, COR, COOH, CONHR, where R is hydrogen or alkyl; halogen and hydroxy;
R4 and R5 are each independently selected from the group consisting of H, alkyl and halogen;
R6-R10 are each independently selected from the group consisting of H, alkyl, halogen, (per)haloalkyl, CN, $NO_2$, COR, COOH, CONHR, $NR_2$, $NHCOCH_3$, $NHCOCF_3$, NHCOR, NHCONHR, NHCOOR, OCONHR, CONHR, where R is as defined above; $NHCSCH_3$, alkylthio, alkylsulfinyl and alkylsulfonyl and R7 and R8 may each independently be further selected from methoxy; provided that at least one of R6-R10 is other than H;
X is selected from the group consisting of O, S, S(O), $SO_2$, NR12, where R12 is selected from the group consisting of H, alkyl, $COCH_3$ and COR, where R is as defined above; and
R11 is selected from the group consisting of alkyl, alkenyl, (per)haloalkyl, haloalkenyl, alkyl-CN and an aryl, heteroaryl, aliphatic or heteroaliphatic, 5-7-membered ring optionally substituted with 1-5 substituents selected from the group consisting of alkyl, halogen, (per)haloalkyl, CN, $NO_2$, COR, COOH, CONHR, $NR_2$, $NHCOCH_3$, $NHCOCF_3$, NHCOR, NHCONHR, NHCOOR, OCONHR, $NHSO_2R$, where R is as defined above; $NHCSCH_3$, alkylthio, alkylsulfinyl and alkylsulfonyl.

2. Arylamide derivative according to claim 1, where R4 and R5 are H and R1 is H, alkyl or halogen.

3. Arylamide derivative according to claim 1, where R1, R4 and R5 are H; R2 is selected from the group consisting of halogen and trifluoromethyl; R3 is selected from the group consisting of $NO_2$, $CONH_2$ and CN; R6, R7 and R10 are H; R8 and R9 are selected from the group consisting of H, halogen and trifluoromethyl, provided that at least one of R8 and R9 is other than H; X is selected from the group consisting of O and $SO_2$; and R11 is selected from the group consisting of alkyl containing up to 6 carbon atoms, phenyl optionally substituted with 1 or 2 halogen atoms or with 1 halogen atom and a further substituent selected from the group consisting of CN, $NO_2$, CONHR, NHCOR, $NHSO_2R$, where R is as defined in claim 1, and alkylsulfonyl; and furyl.

4. Arylamide derivative according to claim 3, where R1, R4 and R5 are H; R2 is trifluoromethyl; R3 is CN; R6, R7 and R10 are H; R8 is trifluoromethyl; R9 is H; X is $SO_2$; and R11 is alkyl containing up to 4 carbon atoms.

5. Arylamide derivative according to claim 3, where R1, R4 and R5 are H; R2 is chloro; R3 is CN; R6, R7 and R10 are H; R8 is trifluoromethyl; R9 is H; X is $SO_2$; and R11 is 4-fluorophenyl.

6. Arylamide derivative according to claim 1, where R8 and R9 are both halogens or one of R8 and R9 is halogen and the other is selected from the group consisting of CN, $NO_2$, CONHR, NHCOR, $NHSO_2R$ and alkylsulfonyl.

7. Arylamide derivative according to claim 1 having formula (I-a)

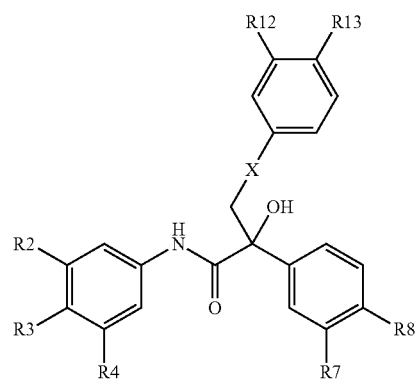

(I-a)

wherein R2, R3, R4, R7, and R8 are as defined in claim 1, and R12 and R13 are each independently selected from the group consisting of H, halo, cyano, and (per)haloalkyl,
or a pharmaceutically acceptable salt thereof.

8. Arylamide derivative according to claim 1 having formula (I-b)

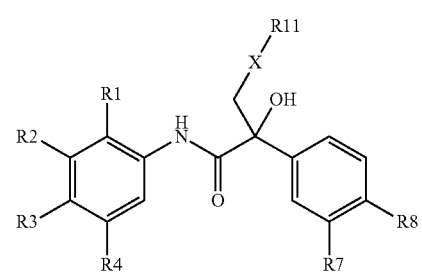

(I-b)

wherein R1, R2, R3, R4, R7, and R8 are as defined in claim 1, and R11 is as defined in claim 1,
or a pharmaceutically acceptable salt thereof.

9. Arylamide derivative according to claim 1 having formula (I-c)

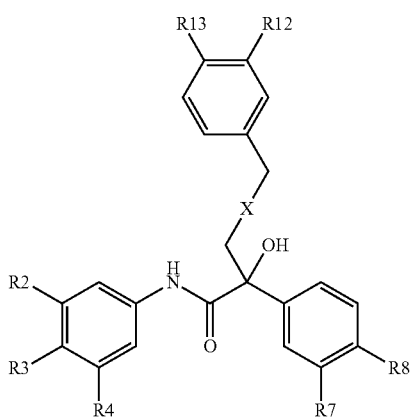

wherein R2, R3, R4, R7, and R8 are as defined in claim 1, and R12 and R13 are each independently selected from the group consisting of H, halo, cyano, and (per)haloalkyl, or a pharmaceutically acceptable salt thereof.

10. Arylamide derivative according to claim 1, where the arylamide derivative is selected from the group consisting of:

N-[4-cyano-3-(trifluoro-methyl)phenyl]-3-(ethanesulfonyl)-2-(4-fluorophenyl)-2-hydroxy-propanamide;

N-[4-cyano-3-(trifluoro-methyl)phenyl]-2-(4-fluorophenyl)-2-hydroxy-3-[(3-methylbutane)-sulfonyl]propanamide;

N-[4-cyano-3-(trifluoro-methyl)phenyl]-3-[(furan-2-ylmethane)sulfonyl]-2-hydroxy-2-[4-(trifluoro-methyl)phenyl]propanamide;

N-(3-chloro-4-cyano-phenyl)-3-[(4-fluoro-benzene)sulfonyl]-2-hydroxy-2-[4-(trifluoro-methyl)phenyl]propanamide;

N-(3-chloro-4-cyanophenyl)-2-(3,4-difluorophenyl)-3-(ethanesulfonyl)-2-hydroxy-propanamide;

N-(3-chloro-4-cyanophenyl)-3-[(3,4-difluorobenzene)sulfonyl]-2-(4-fluorophenyl)-2-hydroxypropanamide;

N-(3-chloro-4-cyanophenyl)-3-(ethanesulfonyl)-2-(4-fluorophenyl)-2-hydroxypropanamide;

N-(3-chloro-4-cyanophenyl)-3-[(3,4-difluorobenzene)sulfonyl]-2-hydroxy-2-[4-(trifluoromethyl)phenyl]propanamide;

N-(3-chloro-4-nitrophenyl)-3-[(4-fluorobenzene)sulfonyl]-2-hydroxy-2-[4-(trifluoromethyl)phenyl]propanamide;

N-(3-chloro-4-nitrophenyl)-3-[(3,4-difluorobenzene)sulfonyl]-2-hydroxy-2-[4-(trifluoromethyl)phenyl]propanamide;

N-(4-nitro-3-trifluoromethylphenyl)-3-[(4-cyano-3-fluorobenzene)sulfonyl]-2-(4-fluorophenyl)-2-hydroxypropanamide;

N-(4-nitro-3-trifluoromethylphenyl)-3-[(4-cyano-3-fluorobenzene)sulfonyl]-2-(4-chlorophenyl)-2-hydroxypropanamide;

N-[4-cyano-3-(trifluoromethyl)phenyl]-3-(ethanesulfonyl)-2-[4-(trifluoromethyl)phenyl]-2-hydroxypropanamide;

N-(3-chloro-4-cyanophenyl)-3-[(4-chlorobenzene)sulfonyl]-2-(4-chlorophenyl)-2-hydroxypropanamide;

N-(3-chloro-4-nitrophenyl)-3-[(4-cyano,3-fluorobenzene)sulfonyl]-2-hydroxy-2-[4-(trifluoromethyl)phenyl]propanamide;

N-(3-chloro-4-cyanophenyl)-3-[(4-chlorobenzene)sulfonyl]-2-hydroxy-2-[4-(trifluoromethyl)phenyl]propanamide;

N-(4-cyano-3-(trifluoromethyl)phenyl)-3-[(4-fluorobenzene)sulfonyl]-2-hydroxy-2-[4-(trifluoromethyl)phenyl]propanamide;

N-(4-cyano-3-(trifluoromethyl)phenyl)-3-[(3,4-difluorobenzene)sulfonyl]-2-hydroxy-2-[3-fluoro-4-(methoxy)phenyl]propanamide;

N-(3-chloro-4-cyanophenyl)-3-(ethanesulfonyl)-2-hydroxy-2-[4-(chlorophenyl]propanamide;

N-(3-chloro-4-cyanophenyl)-2-((3-fluoro-4-methoxy)phenyl)-3-(ethanesulfonyl)-2-hydroxypropanamide;

N-[3-chloro-4-cyanophenyl]-3-{[(4-fluorophenyl)methane]sulfonyl}-2-hydroxy-2-[4-(chloro)phenyl]propanamide;

N-[3-chloro-4-cyanophenyl]-3-{[(4-chlorophenyl)methane]sulfonyl}-2-hydroxy-2-[4-(chloro)phenyl]propanamide;

N-[4-cyano-3-(trifluoromethyl)phenyl]-3-(ethanesulfonyl)-2-(4-chlorophenyl)-2-hydroxypropanamide;

N-(3-chloro-4-cyanophenyl)-3-{[(4-chlorophenyl)methane]sulfonyl}-2-hydroxy-2-[4-(trifluoromethyl)phenyl]propanamide;

N-(3-chloro-4-cyanophenyl)-2-(3-fluoro-4-methoxyphenyl)-3-{[(4-fluorophenyl)methane]sulfonyl}-2-hydroxypropanamide;

N-(3-chloro-4-cyanophenyl)-2-(3-fluoro-4-methoxyphenyl)-3-[(3-fluorobenzene)sulfonyl]-2-hydroxypropanamide;

N-[4-cyano-3-(trifluoromethyl)phenyl]-2-(3,4-difluorophenyl)-3-(ethanesulfonyl)-2-hydroxypropanamide;

N-(3-chloro-4-cyanophenyl)-3-(ethanesulfonyl)-2-hydroxy-2-[3-(trifluoromethyl)phenyl]propanamide;

N-(3-chloro-4-cyanophenyl)-3-{[(4-chlorophenyl)methane]sulfonyl}-2-(3-fluoro-4-methoxyphenyl)-2-hydroxypropanamide;

N-(3-chloro-4-cyanophenyl)-3-[(3-fluorobenzene)sulfonyl]-2-hydroxy-2-[3-(trifluoromethyl)phenyl]propanamide;

N-(3-chloro-4-cyanophenyl)-2-(3,4-difluorophenyl)-3-[(3-fluorobenzene)sulfonyl]-2-hydroxypropanamide;

N-[4-cyano-3-(trifluoromethyl)phenyl]-2-(3,4-difluorophenyl)-3-[(3-fluorobenzene)sulfonyl]-2-hydroxypropanamide;

N-(3-chloro-4-cyanophenyl)-3-{[(4-chlorophenyl)methane]sulfonyl}-2-hydroxy-2-[3-(trifluoromethyl)phenyl]propanamide;

N-(3-chloro-4-cyanophenyl)-3-{[(4-chlorophenyl)methane]sulfonyl}-2-hydroxy-2-[3-(trifluoromethyl)phenyl]propanamide;

N-(3-chloro-4-cyanophenyl)-2-(3,4-difluorophenyl)-3-[(4-fluorobenzene)sulfonyl]-2-hydroxypropanamide;

N-(3-chloro-4-cyanophenyl)-2-(3,4-difluorophenyl)-3-{[(4-fluorophenyl)methane]sulfonyl}-2-hydroxypropanamide;

N-(3-chloro-4-cyanophenyl)-3-{[(4-chlorophenyl)methane]sulfonyl}-2-(3,4-difluorophenyl)-2-hydroxypropanamide;

N-[4-cyano-3-(trifluoromethyl)phenyl]-2-(4-fluorophenyl)-2-hydroxy-3-(propane-1-sulfinyl)propanamide;

N-[4-cyano-3-(trifluoromethyl)phenyl]-2-(4-fluorophenyl)-2-hydroxy-3-(propane-1-sulfonyl)propanamide;

N-(3-chloro-4-cyano-2-fluorophenyl)-2-(3,4-difluorophenyl)-3-(ethanesulfonyl)-2-hydroxypropanamide;

and pharmaceutically acceptable salts thereof.

11. A pharmaceutical composition comprising an effective amount of one or more arylamide derivatives or pharmaceutically acceptable salts thereof according to claim 1 together with a suitable carrier and conventional excipients.

12. A method for treating an androgen receptor related disorder comprising administering to a subject in need thereof a therapeutically effective amount of an arylamide derivative of formula (I) or a pharmaceutically acceptable salt thereof as defined in claim 1, wherein said androgen receptor related disorder is selected from the group consisting of benign prostate hyperplasia, prostate cancer and castration-resistant prostate cancer.

13. The method according to claim 12, where the androgen receptor related disorder is benign prostate hyperplasia.

14. The method according to claim 12, wherein the androgen receptor related disorder is selected from the group consisting of prostate cancer and castration-resistant prostate cancer.

15. The method according to claim 12, where the administration is carried out in combination with another active agent.

16. A process for preparing an arylamide derivative of formula (I) as defined in claim 1, where X is O, SO or $SO_2$, comprising reacting an epoxy compound of formula (5),

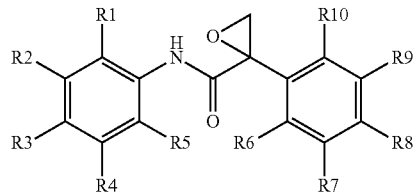

where R1-R10 are as defined in claim 1, with a compound of formula (II),

where R11, R', R" and z are as defined in claim 1 and X' is O or S, to obtain a compound of formula (I), where X is O or S, and, if desired, oxidizing the obtained compound to obtain a compound of formula (I), where X is SO or $SO_2$.

* * * * *